United States Patent

Matsunaga

[11] Patent Number: 5,863,932
[45] Date of Patent: Jan. 26, 1999

[54] MICROBICIDAL COMPOSITION

[75] Inventor: Rei Matsunaga, Kobe, Japan

[73] Assignee: Sumitomo Chemical Company, Limited, Osaka-fu, Japan

[21] Appl. No.: 812,503

[22] Filed: Mar. 7, 1997

[30] Foreign Application Priority Data

Mar. 8, 1996 [JP] Japan ........................ 8-051769

[51] Int. Cl.⁶ .......................... A01N 37/52; A01N 43/64; A01N 55/00
[52] U.S. Cl. ............................ 514/383; 514/63; 514/508
[58] Field of Search ........................ 514/508, 383, 514/63

[56] References Cited

U.S. PATENT DOCUMENTS 5,563,159  10/1996  Kusaba et al. ........................ 514/346

FOREIGN PATENT DOCUMENTS

0656351A1  6/1995  European Pat. Off. .

OTHER PUBLICATIONS

Tom Lin, "The Pesticide Manual Incorporating The Agrochemicals Handbook" 10$^{th}$ Ed. (1995) pp. 942 & 943.

*Primary Examiner*—Allen J. Robinson
*Attorney, Agent, or Firm*—Birch, Stewart, Kolasch & Birch, LLP

[57] ABSTRACT

There is disclosed a microbicidal composition comprising as active ingredients:

(I) a dithiocarbonimide compound represented by the general formula:

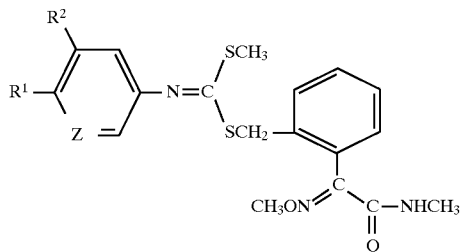

wherein Z represents CH group or nitrogen, $R^1$ and $R^2$ are the same or different and represent hydrogen, $C_1$–$C_6$ alkyl group, halogen, $C_1$–$C_6$ alkoxy group, $C_1$–$C_6$ haloalkyl group or $C_1$–$C_6$ haloalkoxy group, or $R^1$ and $R^2$ are taken together to form methylenedioxy group optionally substituted with fluorine, and (II) at least one compound selected from the group consisting of azole microbicidal compound, cyclic amine microbicidal compound, N-(3,5-dichlorophenyl)imide microbicidal compound, anilinopyrimidine microbicidal compound, cyanopyrrole microbicidal compound, benzimidazole microbicidal compound, fluazinam, thiram and sulfur.

8 Claims, No Drawings

MICROBICIDAL COMPOSITION

FIELD OF THE INVENTION

The present invention relates to a microbicidal composition. More particularly, the present invention relates to a microbicidal composition which is used for agriculture and horticulture.

BACKGROUND OF THE INVENTION

There have been hitherto known many microbicidal compositions. However, the kind of the disease damages to be controlled is very large and it is difficult to actually specify the kind of the disease damage, select the suitable microbicidal agent thereto and control the damage. In addition, the microbicidal agent has to deal with the new disease damages derived from the change in agricultural form. For these reasons, there is a need for a microbicidal composition having the high activity and wide microbicidal spectrum.

OBJECTS OF THE INVENTION

A main object of the invention is to provide a microbicidal composition having the high activity and wide antimicrobicidal spectrum.

This object as well as other objects and advantages of the present invention will become apparent to those skilled in the art from the following description.

SUMMARY OF THE INVENTION

The present invention is to solve the above problems and provides a microbicidal composition comprising as active ingredients:

(I) a dithiocarbonimide compound (hereinafter referred to as "Compound (I)") represented by the general formula:

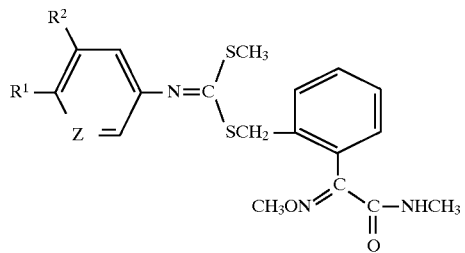

wherein Z represents CH group or nitrogen, $R^1$ and $R^2$ are the same or different and represent hydrogen, $C_1$–$C_6$ alkyl group, halogen, $C_1$–$C_6$ alkoxy group, $C_1$–$C_6$ haloalkyl group or $C_1$–$C_6$ haloalkoxy group, or $R^1$ and $R^2$ are taken together to form methylenedioxy group optionally substituted with fluorine, and (II) at least one compound (hereinafter referred to as "Compound (II)") selected from the group consisting of azole microbicidal compounds, cyclic amine microbicidal compounds, N-(3,5-dichlorophenyl)imide microbicidal compounds, anilinopyrimidine microbicidal compounds, cyanopyrrole microbicidal compounds, benzimidazole microbicidal compounds, fluazinam, thiram and sulfur.

DETAILED DESCRIPTION OF THE INVENTION

At first, Compound (I) is explained.

In the above general formula, examples of $C_1$–$C_6$ alkyl group represented by $R^1$ and $R^2$ include methyl group and ethyl group. Examples of halogen include fluorine and chlorine. Examples of $C_1$–$C_6$ alkoxy group include methoxy group and ethoxy group. Examples of $C_1$–$C_6$ haloalkyl group include trifluoromethyl group. Examples of $C_1$–$C_6$ haloalkoxy group include trifluoromethoxy group.

Compound (I) can be prepared by a method described In EP-A-0656351.

The embodiments of Compound (I) are shown together with the compound numbers in Table 1 (The embodiments are shown by the definition of respective substituents in the compound represented by the above general formula).

TABLE 1

| Compound No. | Z | $R^1$ | $R^2$ |
|---|---|---|---|
| (Ia) | CH | $CH_3$ | H |
| (Ib) | CH | $C_2H_5$ | H |
| (Ic) | CH | $OC_2H_5$ | H |
| (Id) | CH | $CF_3$ | H |
| (Ie) | CH | $OC_2H_5$ | F |
| (If) | CH | $OCF_2O$ | |
| (Ig) | N | $OC_2H_5$ | H |
| (Ih) | CH | $CF_3O$ | H |

Then, Compound (II) is explained. Each page described after the name of each compound represents the page where each compound is described in "The Pesticide Manual, Tenth Edition (edited by Clive Tomlin, published by The British Crop Protection Council and The Royal Society of Chemistry, 1994)".

In the present invention, the azole microbicidal compound means a microbicidal compound having a triazole ring or an imidazole ring, such as 1-[[2-(2,4-dichlorophenyl)-4-propyl-1,3-dioxolan-2-yl]methyl]-1H-1,2,4-triazole {propiconazole, page 855}, β-(4-chlorophenoxy)-α-(1,1-dimethylethyl)-1H-1,2,4-triazol-1-ethanol {triadimenol, page 1001}, 1-(N-propyl-N-[2-(2,4,6-trichlorophenoxy)ethyl]}carbamoylimidazole {prochloraz, page 832}, 1-[2-(2,4-dichlorophenyl)pentyl]-1H-1,2,4-triazole {penconazole, page 776}, 1-(4-chlorophenyl)-4,4-dimethyl-3-(1H-1,2,4-triazol-1-ylmethyl)pentan-3-ol {tebuconazole, page 942}, 1-[[bis(4-fluorophenyl)methylsilyl]methyl]-1H-1,2,4-triazole {flusilazole, page 510}, (E)-1-(2,4-dichlorophenyl)-4,4-dimethyl-2-(1H-1,2,4-triazol-1-yl)-pent-1-ene-3-ol (diniconazole, page 356), 1-[[4-bromo-2-(2,4-dichlorophenyl)tetrahydro-2-furanyl]methyl]-1H-1,2,4-triazole {bromuconazole, page 124}, cis-1-[[3-(2-chlorophenyl)-2-(4-fluorophenyl)oxiranyl]methyl]-1H-1,2,4-triazole (epoxyconazole, BAS480F, page 67), 3-chloro-4-[4-methyl-2-(1H-1,2,4-triazol-1-ylmethyl)-1,3-dioxolan-2-yl]phenyl 4-chlorophenyl ether {difenoconazole, page 328}, 2-(4-chlorophenyl)-3-cyclopropyl-1-(1H-1,2,4-triazol-1-yl)butan-2-ol{cyproconazole, page 268}, 5-[(4-chlorphenyl)methyl]-2,2-dimethyl-1-(1H-1,2,4-triazol-1-ylmethyl)cyclopentanol {metconazole, page 669}, (E)-4-chloro-α, α, α-trifluoro-N-(1-imidazol-1-yl-2-propoxyethylidene)-o-toluidine {triflumizole, page 1022}, 2-(2,4-dichlorophenyl)-3-(1H-1,2,4-triazol-1-yl)propyl 1,1,2,2-tetrafluoroethyl ether {tetraconazole, page 965}, 2-(4-chlorphenyl)-2-(1H-1,2,4-triazol-1-ylmethyl)-hexanenitrile {myclobutanil, page 712}, 4-(4-chlorophenyl)-2-phenyl-2-(1H-1,2,4-triazol-1-ylmethyl)butyronitrile (fenbuconazole, page 428}, 2-(2,4-dichlorophenyl)-1-(1H-1,2,4-triazol-1-yl) hexan-2-ol {hexaconazole, page 562}, 3-(2,4-dichlorophenyl)-6-fluoro-2-(1H-1,2,4-triazol-1-yl)quinazolin-4(3H)-one {fluquinconazole, page 498}, (E)-5-(4-chlorobenzylidene)-2,2-dimethyl-1-(1H-1,2,4-triazol-1-ylmethyl)cyclopentanol {triticonazole, page 1033}, 1-(biphenyl-4-yloxy)-3,3-dimethyl-1-(1H-1,2,4-triazol-1- yl)butan-2-ol {bitertanol, page 106}, 1-[2-(2,4-dichlorophenyl)-2-(2-propenyloxy)ethyl]-1H-imidazol {imazalil, page 580} and 2,4'-difluoro-α-(1H-1,2,4-triazol-1-ylmethyl)benzhydrylalcohol {flutriafol, page 514}.

The cyclic amine microbicidal compound means a compound having the 4-substituted-2,6-dimethylmorpholine structure, such as cis-4-[3-(4-tert-butylphenyl)-2-methylpropyl]-2,6-dimethylmorpholine {fenpropimorph, page 448} and 2,6-dimethyl-4-tridecylmorpholine {tridemorph, page 1019}, and a microbicidal compound having the N-substituted-piperidine structure, such as 1-[3-(4-tert-butylphenyl)-2-methylpropyl]piperidine {fenpropidin, page 447}.

The N-(3,5-dichlorophenyl}imide microbicidal compound means a microbicidal compound having the N-(3,5-dichlorophenyl)imide structure, such as N-(3,5-dichlorophenyl)-1,2-dimethylcyclopropane-1,2-dicarboximide {procymidone, page 834}, 3-(3,5-dichlorophenyl)-5-methyl-5-vinyl-1,3-oxazolidin-2,4-dione {vinclozolin, page 1041} and 3-(3,5-dichlorophenyl)-N-(1-methylethyl)-2,4-dioxo-1-imidazolidinecarboxamide {iprodione, page 603}.

The anilinopyrimidine microbicidal compound means a microbicidal compound having the anilinopyrimidine structure, such as N-(4,6-dimethylpyrimidin-2-yl)aniline {pyrimethanil, page 885}, N-(4-methyl-6-prop-1-ynylpyrimidin-2-yl)aniline (mepanipyrim, page 652) and 4-cyclopropyl-6-methyl-N-phenylpyrimidine-2-amine {cyprodinil, CGA219417, page 161}.

The cyanopyrrole microbicidal compound means a microbicidal compound having the 3-cyano-4-phenylpyrrole structure, such as 4-(2,2-difluoro-1,3-benzodioxol-4-yl)-pyrrole-3-carbonitrile {fludioxonil, page 482} and 4-(2,3-dichlorophenyl)pyrrole-3-carbonitrile {fenpiclonil, page 444}.

The benzimidazole microbicidal compound means a microbicidal compound having the benzimidazole structure or having that structure when metabolized, such as methyl benzimidazol-2-ylcarbamate {carbendazim, page 149}, methyl 1-(butylcarbamoyl)benzimidazol-2-ylcarbamate {benomyl, page 82} and dimethyl [1,2-phenylenebis-(iminocarbonothioyl)]bis[carbamate] {thiophanate-methyl, page 987}.

Fluazinam means 3-chloro-N-(3-chloro-5-trifluoromethyl-2-pyridyl)-α, α, α-trifluoro-2,6-dinitro-p-fluidine (page 474).

Thiram means bis(dimethylthiocarbamoyl)disulfide (page 989).

Examples of the vegetable disease damages which can be controlled by the present invention are blast (*Pyricularia oryzae*), leaf spot (*Cochliobolus miyabeanus*) and sheath blight (*Rhizoctonia solani*) of rice plant, powdery mildew (*Erysiphe graminis, f. sp.hordei, f. sp.tritici*), scab (*Gibberella zeae*), rust (*Puccinia striiformis, P. graminis, P. recondita, P. hordei*), snow blight (*Typhula sp. Micronectriella nivalis*), loose smut (*Ustilago tritici, U. nuda*), bunt (*Tilletia caries*), eyespot (*Pseudocercosporella herpotrichoides*), foot rot (*Rhizoctonia cerealis*), leaf blotch (*Rhynchosporium secalis*), leaf blight (*Sentoria tritici*) and glume blotch (*Leptosphaeria nodorum*) of cereal, melanosa (*Diaporthe citri*), scab (*Elsinoe fawcetti*), blue mold (*Penicillium digitatum*) and green mold (*P. italicum*) of oranges, blossom blight (*Sclerotinia mali*), canker (*Valsa mali*), powdery mildew (*Podosphaera leucotricha*), alternaria blotch (*Alternaria mali*) and scab (*Venturia inaequalis*) of apple, scab (*Venturia nashicola*), black spot (*Alternaria kikuchiana*) and rust (*Gymnosporangium haraeanum*) of pear, brown rot (*Sclerotinia cinerea*), scab (*Cladosporium carpophilum*) and phomopsis rot (*Phomopsis sp.*) of peach, downy mildew (*Plasmopara viticola*), anthracnose (*Elsinoe ampelina*), ripe rot (*Glomerella cingulata*), powdery mildew (*Uncinula necator*) and rust (*Phakopsora ampelopsidis*) of grape, anthracnose (*Gloeosporium kaki*) and angular leaf spot (*Cercospora kaki, Mycosphaerelle nawae*) of persimmon, downy mildew (*Pseudoperonospora cubensis*), anthracnose (*Colletotrichum lagenarium*), powdery mildew (*Sphaerotheca fuliginea*) and gummy stem blight (*Mycosphaerella melonis*) of Cucurbit, early blight (*Alternaria solani*), leaf mold (*Cladosporium fulvum*) and late blight (*Phytophthora infestans*) of tomato, brown spot (*Phomopsis vexans*) and powdery mildew (*Erysiphe cichoracearum*) of egg plant, alternaria leaf spot (*Alternaria japonica*) and white spot (*Cercosporella brassicae*) of Crucifer, rust (*Puccinia allii*) of Welsh onion, purple stain (*Cercospora kikuchii*), sphaceloma scab (*Elsinoe glycines*) and melanose (*Diaporthe phaseolorum var. sajae*) of soybean, anthracnose (*Collectotrichum lindemuthianum*) of kidney bean, early leaf spot (*Mycosphaerella personatum*) and late leaf spot (*Cercospora arachidicola*) of peanut, powdery mildew (*Erysiphe pisi*) and downy mildew (*Peronospora pisi*) of garden pea, downy mildew (*Peronospora viciae*) and late blight (*Phytophthora nicotianae*) of broad bean, early blight (*Alternaria solani*) and late blight (*Phytophthora infestans*) of potato, powdery mildew (*Sphaerotheca humuli*) and late blight (*Phytophthora nicotianae*) of strawberry, net blister blight (*Exobasidium reticulatum*) and white scab (*Elsinoe leucospila*) of tea, brown spot (*Alternaria longpipes*), powdery mildew (*Erysiphe cichoracearum*), anthracnose (*Collectotrichum tabacum*) and late blight (*Phytophthora parasitica*) of tobacco, cercospora leaf spot (*Cercospora beticola*) of beet, black spot (*Diplocarpon rosae*), powdery mildew (*Sphaerotheca pannosa*) and late blight (*Phytophthora megasperma*) of rose, leaf blight (*Septoria chrysanthemiindici*) and white rust (*Puccinia horiana*) of chrysanthemum, and gray mold (*Botrytis cinerea*) and sclerotinia rot (*Sclerotinia sclerotiorum*) of various crops.

In the microbicidal composition of the present invention, a mixing ratio of Compound (I) and Compound (II) is not limited to specified one. An amount of at least one compound selected from azole compounds, cyclic amine compounds, N-(3,5-dichlorophenyl)imide compounds, anilinopyrimidine compounds, cyanopyrrole compounds, benzimidazole compounds and fluazinam is usually in a range of 0.01 to 100 parts by weight, preferably 0.05 to 50 parts by weight based on 1 part by weight of Compound (I). An amount of thiram is usually in a range of 0.01 to 1000 parts by weight, preferably 0.1 to 500 parts by weight based on 1 part by weight of Compound (I). An amount of sulfur is usually in a range of 1 to 5000 parts by weight, preferably 5 to 1000 parts by weight based on 1 part by weight of Compound (I).

The microbicidal composition of the present invention can be used merely by mixing Compound (I) and Compound (II). However, the microbicidal composition of the present invention is usually used by formulating into preparations such as water dispersible powder, suspension, granule, dry-flowable agent, emulsifiable concentrate, liquid formulation, oil solution, smoking agent, aerosol agent and microcapsule, by mixing Compound (I) and Compound (II), mixing the mixture with solid carrier, liquid carrier and/or gaseous carrier and, if necessary, adding thereto an adjuvant for preparations such as surfactant, adhesive agent, dispersing agent and stabilizing agent. Alternatively, the microbicidal composition of the present invention is used by formulating Compound (I) and Compound (II) into preparations separately, diluting each preparation with water, if necessary, and mixing both preparations. A total amount of the active ingredient compounds contained in these preparations is usually 0.1 to 99% by weight, preferably 0.2 to 90% by weight.

Examples of the solid carrier are pulverized or particulate clay (such as kaolin clay, diatomaceous earth, synthetic hydrated silicon oxide, attapulgite clay, bentonite and acid clay), talcs, other inorganic minerals (such as sericite, quartz powder, sulfur powder, activated carbon, calcium carbonate and hydrated silica), and salt for chemical fertilizer (such as ammonium sulfate, ammonium phosphate, ammonium nitrate, urea and ammonium chloride). Examples of the liquid carrier are water, alcohols (such as methanol and ethanol), ketones (such as acetone, methyl ethyl ketone and cyclohexanone), aromatic hydrocarbons (such as benzene, toluene, xylene, ethylbenzene and methylnaphthalene), aliphatic hydrocarbons (such as hexane and kerosene), esters (such as ethyl acetate and butyl acetate), nitriles (such as acetonitrile and isobutyronitrile), ethers (such as dioxane and diisopropyl ether), acid amides (such as dimethylformamide and dimethylacetamide), halogenated hydrocarbons (such as dichloroethane, trichloroethylene and carbon tetrachloride). Examples of the gaseous carrier are butane gas, carbonic acid gas and fluorocarbon gas.

Examples of the surfactant are alkylsulfuric esters, alkylsulfonate, alkylarylsulfonate, alkyl aryl ether and its polyoxyethylene compound, polyethylene glycol ether, multivalent alcohol ester and sugar alcohol derivative.

Examples of the adhesive agent and the dispersing agent are casein, gelatin, polysaccharides (such as starch, acacia, cellulose derivative and alginic acid), lignin derivative, bentonite, sugars, and synthetic water-soluble polymer (polyvinyl alcohol, polyvinyl pyrrolidone and polyacrylic acid). Examples of the stabilizing agent are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oil, mineral oil, and fatty acid or ester thereof.

The above-described preparations are applied to plants or soil as they are or by diluting with water or the like. When the preparations are applied to soil, they may be sprayed to the surface of soil or may be used by applying in admixture with the soil. Alternatively, the preparations may be applied by various methods such as seed treatment method and ULV method. When the preparations are used as a seed treating agent, they are used by seed coating treatment, seed soaking treatment, seed spraying treatment or the like.

The microbicidal composition of the present invention may be used together with other microbicidal agent, insecticide, acaricide, nematicide, herbicide, seed disinfectant, fertilizer, soil conditioner and the like.

An amount of application of the microbicidal composition of the present invention depends upon kind of the active ingredient compound, mixing ratio of Compound (I) and Compound (II), weather conditions, preparation form, application time, application method, application place, subject disease damage, subject crop and the like and a total amount of the active ingredient compounds is usually 0.001 to 1000 g/are, preferably 0.1 to 100 g/are. When emulsifiable concentrate, water dispersible powder, suspension, liquid formulation or the like is applied by diluting, for example, with water, the application concentration is usually 0.0001 to 1% by weight, preferably 0.001 to 0.5% by weight. Granule, powder or the like is applied as it is without dilution. Upon seed treatment, the total amount of active ingredient compounds to be applied is usually 0.001 to 50 g/kg seed, preferably 0.01 to 10 g/kg seed.

The following Preparation Examples and Test Examples illustrate the present invention in detail but are not to be construed to limit the scope thereof.

"Part" means "part by weight" unless otherwise indicated.

PREPARATION EXAMPLE 1

One part of Compound (Ia), (Ib), (Ic), (Id), (Ie), (If), (Ig) or (Ih); 5 parts of propiconazole, triadimenol, prochloraz, penconazole, tebuconazole, flusilazole, diniconazole, bromuconazole, epoxyconazole, difenconazole, cyproconazole, metconazole, triflumizole, tetraconazole, myclobutanil, fenbuconazole, hexaconazole, fluquinconazole, triticonazole, bitertanol, imazalil, flutriafol, fenpropimorph, tridemorph, fenpropidin, procymidone, vinclozolin, iprodione, pyrimethanil, mepanipyrium, cyprodinil, fludioxonil, fenpiclonil, carbendazim, benomyl, thiophanate-methyl, fluazinam, thiram or sulfur: one part of synthetic hydrated silicon oxide; 2 parts of calcium lignin sulfonate; 30 parts of bentonite and 61 parts of kaolin clay are well ground and mixed, water is added thereto to well knead together, followed by granulation and drying to obtain granules.

PREPARATION EXAMPLE 2

5 Parts of Compound (Ia), (Ib), (Ic), (Id), (Ie), (If), (Ig) or (Ih); 5 parts of propiconazole, triadimenol, prochloraz, penconazole, tebuconazole, flusilazole, diniconazole, bromuconazole, epoxyconazole, difenconazole, cyproconazole, metconazole, triflumizole, tetraconazole, myclobutanil, fenbuconazole, hexaconazole, fluquinconazole, triticonazole, bitertanol, imazalil, flutriafol, fenpropimorph, tridemorph, fenpropidin, procymidone, vinclozolin, iprodione, pyrimethanil, mepanipyrium, cyprodinil, fludioxonil, fenpiclonil, carbendazim, benomyl, thiophanate-methyl, fluazinam, thiram or sulfur; one part of synthetic hydrated silicon oxide; 2 parts of calcium lignin sulfonate; 30 parts of bentonite and 57 parts of kaolin clay are well ground and mixed, water is added thereto to well knead together, followed by granulation and drying to obtain granules.

PREPARATION EXAMPLE 3

0.5 Part of Compound (Ia), (Ib), (Ic), (Id), (Ie), (If), (Ig) or (Ih); 2.5 parts of propiconazole, triadimenol, prochloraz, penconazole, tebuconazole, flusilazole, diniconazole, bromuconazole, epoxyconazole, difenconazole, cyproconazole, metconazole, triflumizole, tetraconazole, myclobutanil, fenbuconazole, hexaconazole, fluquinconazole, triticonazole, bitertanol, imazalil, flutriafol, fenpropimorph, tridemorph, fenpropidin, procymidone, vinclozolin, iprodione, pyrimethanil, mepanipyrium, cyprodinil, fludioxonil, fenpiclonil, carbendazim, benomyl, thiophanate-methyl, fluazinam, thiram or sulfur; 86 parts of kaolin clay and 11 parts of talc are well ground and mixed to obtain powders.

PREPARATION EXAMPLE 4

5 Parts of Compound (Ia), (Ib), (Ic), (Id), (Ie), (If), (Ig) or (Ih); 25 parts of propiconazole, triadimenol, prochloraz, penconazole, tebuconazole, flusilazole, diniconazole, bromuconazole, epoxyconazole, difenconazole, cyproconazole, metconazole, triflumizole, tetraconazole, myclobutanil, fenbuconazole, hexaconazole, fluquinconazole, triticonazole, bitertanol, imazalil, flutriafol, fenpropimorph, tridemorph, fenpropidin, procymidone, vinclozolin, iprodione, pyrimethanil, mepanipyrium, cyprodinil, fludioxonil, fenpiclonil, carbendazim, benomyl, thiophanate-methyl, fluazinam, thiram or sulfur; 3 parts of polyoxyethylene sorbitan monooleate; 3 parts of carboxymethyl cellulose and 64 parts of water are mixed and wet-ground to the particle size of less than 5 microns to obtain suspensions.

PREPARATION EXAMPLE 5

10 Parts of Compound (Ia), (Ib), (Ic), (Id), (Ie), (If), (Ig) or (Ih); 50 parts of propiconazole, triadimenol, prochloraz, penconazole, tebuconazole, flusilazole, diniconazole, bromuconazole, epoxyconazole, difenconazole, cyproconazole, metconazole, triflumizole, tetraconazole, myclobutanil, fenbuconazole, hexaconazole, fluquinconazole, triticonazole, bitertanol, imazalil, flutriafol, fenpropimorph, tridemorph, fenpropidin, procymidone, vinclozolin, iprodione, pyrimethanil, mepanipyrium, cyprodinil, fludioxonil, fenpiclonil, carbendazim, benomyl, thiophanate-methyl, fluazinam, thiram or sulfur; 3 parts of calcium lignin sulfonate; 2 parts of sodium lauryl sulfate and 35 parts of synthetic hydrated silicon oxide are well ground and mixed to obtain water dispersible powders.

The following Test Examples indicate that the microbicidal composition of the present invention has the excellent vegetable disease damage controlling activity.

Controlling effect, which is expected when treatment is carried out by mixing the given two kinds of active ingredient compounds, is generally calculated according to the following Colby equation.

$$E = X + Y - \frac{X \times Y}{100}$$

X: Controlling value (%) when treatment is carried out by using an active ingredient compound A at the concentration of m ppm Y: Controlling value (%) when treatment is carried out by using an active ingredient compound B at the concentration of n ppm E: Controlling value (%) when treatment is carried out by using an active ingredient compound A at the concentration of m ppm and an active ingredient compound B at the concentration of n ppm (hereinafter referred to as "expected controlling value")

If controlling value (%) when treatment is carried out by actually mixing two kinds of active ingredient compounds is greater than expected controlling value (%), it can be said that there is the synergistic effect in a combination of those compounds.

TEST EXAMPLE 1

Wheat rust disease controlling test (preventive effect)

Sandy loam was filled into a plastic pot, wheat (Norin No. 73) was seeded thereto, the wheat was grown for 10 days in a greenhouse. A test preparation, which had formulated into water dispersible powder according to Preparation Example 5, was diluted with water to a predetermined concentration. The diluted test preparation was sprayed to foliage of a wheat seedling having the developed second to third true leaves so as to effectively attach to the leaf. After air drying, the seedling was inoculated with spore of wheat rust, placed in the darkness under high humidity at 23° C. for one day, grown for 6 days under illumination, the severity (%) was investigated and the actual controlling value (%) was obtained according to the following equation.

Controlling value (%)={[Severity of non-treated plant (%)–severity of treated plant (%)]/[severity of non-treated plant (%)]}×100

The results are shown in Table 2

TABLE 2

| Test compound | Concentration of active ingredient (ppm) | Actual controlling value (%) | Expected controlling value (%) |
| --- | --- | --- | --- |
| (Ib) + epoxyconazale | 0.8 + 0.1 | 100 | 80 |
| (Id) + epoxyconazole | 0.8 + 0.1 | 100 | 86 |
| (If) + epoxyconazole | 0.8 + 0.1 | 100 | 80 |
| (Ib) + tebuconazole | 0.8 + 0.1 | 100 | 75 |
| (Id) + tebuconazole | 0.8 + 0.1 | 100 | 83 |
| (If) + tebuconazole | 0.8 + 0.1 | 100 | 75 |
| (Ib) + fenpropimorph | 0.8 + 25 | 100 | 80 |
| (Id) + fenpropimorph | 0.8 + 25 | 100 | 86 |
| (If) + fenpropimorph | 0.8 + 25 | 100 | 75 |
| (Ib) | 0.8 | 50 | — |
| (Id) | 0.8 | 65 | — |
| (If) | 0.8 | 50 | — |
| Epoxyconazole | 0.1 | 60 | — |
| Tebuconazole | 0.1 | 50 | — |
| Fenpropimorph | 25 | 60 | — |

TEST EXAMPLE 2

Pea sclerotinia rot controlling test (preventive effect)

Sandy loam was filled into a plastic pot, pea (Alaska) was seeded thereto, the pea was grown for 10 days in a greenhouse. A test preparation, which had formulated into suspension according to Preparation Example 4, was diluted with water to a predetermined concentration. The diluted test preparation was sprayed to foliage of a pea seedling so as to effectively attach to the leaf plane. After air drying, hypha and sclerotium of sclerotinia rot were mixed with an artificial soil, the mixture was placed at the root of the plant to inoculate the plant. After inoculation, the seedling was placed in a greenhouse at 23° C. for 2 days, the severity (%) was investigated and the actual controlling value (%) was obtained according to the above equation.

The results are shown in Table 3

TABLE 3

| Test compound | Concentration of active ingredient (ppm) | Actual controlling value (%) | Expected controlling value (%) |
| --- | --- | --- | --- |
| (Ib) + procymidone | 250 + 125 | 90 | 63 |
| (Ie) + procymidone | 250 + 125 | 85 | 63 |
| (Ib) + pyrimethanil | 250 + 200 | 75 | 52 |
| (Ie) + pyrimethanil | 250 + 200 | 73 | 52 |
| (Ib) + fludioxonil | 250 + 100 | 78 | 58 |
| (Ie) + fludioxonil | 250 + 100 | 75 | 58 |
| (Ib) + benomyl | 250 + 100 | 85 | 60 |
| (Ie) + benomyl | 250 + 100 | 85 | 60 |

TABLE 3-continued

| Test compound | Concentration of active ingredient (ppm) | Actual controlling value (%) | Expected controlling value (%) |
|---|---|---|---|
| (Ib) + fluazinam | 250 + 125 | 83 | 60 |
| (Ie) + fluazinam | 250 + 125 | 80 | 60 |
| (Ib) + thiram | 250 + 500 | 70 | 52 |
| (Ie) + thiram | 250 + 500 | 70 | 52 |
| (Ib) | 250 | 20 | — |
| (Ie) | 250 | 20 | — |
| Procymidone | 125 | 54 | — |
| Pyrimethanil | 200 | 40 | — |
| Fludioxonil | 100 | 48 | — |
| Benomyl | 100 | 50 | — |
| Fluazinam | 125 | 50 | — |
| Thiram | 500 | 40 | — |

TEST EXAMPLE 3

Peanut early leaf spot disease controlling test (preventive effect)

Sandy loam was filled into a plastic pot, peanut (*Chiba handachisei*) was seeded thereto, the peanut was grown for 20 days in a greenhouse. A test preparation, which had formulated into water dispersible powder according to Preparation Example 5, was diluted with water to a predetermined concentration. The diluted test preparation was sprayed to foliage of a peanut seedling so as to effectively attach to the leaf. After air drying, the seedling was inoculated with spore of peanut early leaf spot, placed under high humidity at 27° C. for 7 days, further grown at 27° C. for 7 days, the severity (%) was investigated and the actual controlling value (%) was obtained according to the above equation.

The results are shown in Table 4

TABLE 4

| Test compound | Concentration of active ingredient (ppm) | Actual controlling value (%) | Expected controlling value (%) |
|---|---|---|---|
| (Ia) + tebuconazole | 3.1 + 3.1 | 100 | 72 |
| (Ib) + tebuconazole | 3.1 + 3.1 | 100 | 79 |
| (Ic) + tebuconazole | 3.1 + 3.1 | 90 | 65 |
| (Ih) + tebuconazole | 3.1 + 3.1 | 100 | 79 |
| (Ia) + diniconazole | 3.1 + 1 | 100 | 76 |
| (Ib) + diniconazole | 3.1 + 1 | 100 | 82 |
| (Ic) + diniconzaole | 3.1 + 1 | 95 | 70 |
| (Ih) + diniconazole | 3.1 + 1 | 100 | 82 |
| (Ia) | 3.1 | 60 | — |
| (Ib) | 3.1 | 70 | — |
| (Ic) | 3.1 | 50 | — |
| (Ih) | 3.1 | 70 | — |
| Tebuconazole | 3.1 | 30 | — |
| Diniconazole | 1 | 40 | — |

TEST EXAMPLE 4

Vine powdery mildew controlling test (preventive effect)

One root of vine (Berry A) was planted in a plastic pot filled with sandy loam. A test preparation, which had formulated into water dispersible powder according to Preparation Example 5, was diluted with water to a predetermined concentration. The diluted test preparation was sprayed to foliage of vine seedling, when the fourth leaf was developed, so as to effectively attach to the leaf plane. After air drying, the leaf was inoculated by spraying a solution of spore of vine powdery mildew ($2 \times 10^6$/ml). After inoculation, the vine was cultivated at 24° C. for three weeks, the severity (%) was investigated and the actual controlling value (%) was obtained according to the above equation.

The results thereof are shown in Table 5.

TABLE 5

| Test compound | Concentration of active ingredient (ppm) | Actual controlling value (%) | Expected controlling value (%) |
|---|---|---|---|
| (Ia) + flusilazole | 1 + 0.2 | 100 | 87 |
| (Ib) + flusilazole | 1 + 0.2 | 100 | 88 |
| (Ig) + flusilazole | 1 + 0.2 | 100 | 87 |
| (Ia) + diniconazole | 1 + 0.1 | 100 | 85 |
| (Ib) + diniconazole | 1 + 0.1 | 100 | 88 |
| (Ig) + diniconazole | 1 + 0.1 | 100 | 85 |
| (Ia) + sulfur | 1 + 250 | 100 | 79 |
| (Ib) + sulfur | 1 + 250 | 100 | 83 |
| (Ig) + sulfur | 1 + 250 | 100 | 79 |
| (Ia) | 1 | 70 | — |
| (Ib) | 1 | 75 | — |
| (Ig) | 1 | 70 | — |
| Flusilazole | 0.2 | 55 | — |
| Diniconazole | 0.1 | 50 | — |
| Sulfur | 250 | 30 | — |

The following Preparation Example illustrates the preparation of Compound (I) used in the present invention Reference Preparation Example [Preparation of Compound (Ie)]

Carbon disulfide (2.0 g, 26 mmol) was added to a mixture of 4-ethoxy-3-fluoroaniline (2.7 g, 17 mmol) and triethylamine (4.0 g, 40 mmol) while stirring. The mixture was stirred at room temperature for 10 hours, N,N-dimethylformamide (30 ml) was added thereto and methyl iodide (2.2 g, 16 mmol) was added dropwise. The mixture was stirred at room temperature for 30 minutes and dilute hydrochloric acid was added thereto, followed by extraction with diethyl ether. The organic layer was washed with a saturated sodium chloride solution, dried with anhydrous sodium sulfate and concentrated under reduced pressure. The residue was subjected to silica gel column chromatography (elution solvent; hexane:ethyl acetate=4:1) to obtain methyl 4-ethoxy-3-fluorophenyldithiocarbamate (2.5 g, 10 mmol) as crystals. m.p. 108.0° C.

Sodium hydride (60% oil dispersion, 60 mg, 1.5 mmol) was added to a solution of 4-ethoxy-3-fluorophenyldithiocarbamate (0.40 g, 1.6 mmol) in tetrahydrofuran (20 ml) at room temperature. The mixture was stirred at room temperature for 30 minutes and (E)-methoximino-2-(2-bromomethylphenyl)-N-methylacetamide (0.42 g, 1.5 mmol) was added thereto. The mixture was stirred at room temperature for 30 minutes and water was added thereto, followed by extraction with ethyl acetate. The organic layer was dried with anhydrous magnesium sulfate and concentrated under reduced pressure. The residue was subjected to silica gel column chromatography (elution solvent, hexane:ethyl acetate=1:1) to obtain (E)-2-methoximino-2-[2-(4-ethoxy-3-fluorophenylimino)(methylthio)methylthiophenyl]-N-methylacetamide (0.60 g, 1.3 mmol) as an oil.

$^1$H-NMR (CDCl$_3$/TMS, δ (ppm)) 1.26 (3H, t, J=7.1 Hz), 2.45 (3H, s), 2.88 (3H, d, J=4.6 Hz), 2.95 (3H, s), 4.12 (2H, q, J=7.1 Hz), 4.22 (2H, br s), 6.55–7.50 (8H, m)

Some NMR data of the other compounds used in the present invention are shown below.

Compound (Ia):
$^1$H-NMR (CDCl$_3$/TMS, δ (ppm)) 2.46 (3H, s), 2.89 (3H, d, J=5.0 Hz), 3.95 (3H, s), 4.21 (2H, br s), 6.51–7.46 (8H, m)

Compound (If):
$^1$H-NMR (CDCl$_3$/TMS, δ (ppm)) 2.31 (3H,s), 2.44 (3H, s), 2.86 (3H, d, J=5.0 Hz), 3.95 (3H, s), 4.22 (2H, br s), 6.72–7.49 (9H, m)

What is claimed is:

1. A microbicidal composition comprising synergistic microbicidally effective amounts of:
   (I) a dithiocarbonimide compound represented by the general formula:

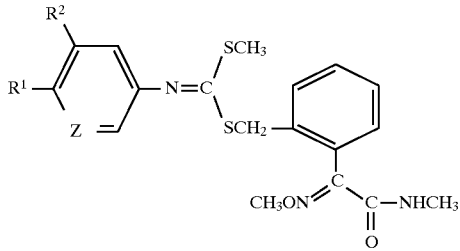

wherein Z represents a CH group, R$^1$ and R$^2$ are the same or different and represent a hydrogen atom, a C$_1$–C$_6$ alkyl group, a halogen atom, a C$_1$–C$_6$ alkoxy group, a C$_1$–C$_6$ haloalkyl group or a C$_1$–C$_6$ haloalkoxy group, and
   (II) a triazole compound selected from the group consisting of tebuconazole, epoxyconazole, diniconazole and flusilazole, wherein ingredient (II) is present in an amount of 0.01 to 100 parts by weight, based on 1 part by weight of (I).

2. The microbicidal composition according to claim 1, wherein said triazole compound is tebuconazole.

3. The microbicidal composition according to claim 1, wherein ingredient (II) is present in an amount of 0.05 to 50 parts by weight based on 1 part by weight of ingredient (I).

4. The microbicidal composition according to claim 1 or 2, wherein in ingredient (I), Z is CH, R$^1$ is a C$_2$H$_5$ group and R$^2$ is a hydrogen atom.

5. A method for controlling agricultural or horticultural noxious microbes, which comprises applying a synergistic microbicidally effective amount of the composition as defined in claim 5, to plants or soil, wherein the total amount of ingredients (I) and (II) is in the range of 0.001 to 1000 g/are.

6. The method for controlling agricultural or horticultural noxious microbes according to claim 5, wherein the total amount of ingredients (I) and (II) is in the range 0.1 to 100 g/are.

7. A method for controlling agricultural or horticultural noxious microbes, which comprises applying a synergistic microbicidally effective amount of the composition as defined in claim 5 to seed in an amount of 0.001 to 50 g/kg seed as the total amount of ingredient (I) and ingredient (II).

8. A method for controlling agricultural or horticultural noxious microbes, which comprises applying a synergistic microbicidally effective amount of the composition as defined in claim 5 to seed in an amount of 0.01 to 10 g/kg seed as the total amount of ingredient (I) and ingredient (II).

* * * * *